United States Patent
Cobb

(10) Patent No.: US 7,047,809 B2
(45) Date of Patent: May 23, 2006

(54) ULTRASONIC MONITOR OF MATERIAL COMPOSITION AND PARTICLE SIZE

(75) Inventor: Wesley N. Cobb, Highlands Ranch, CO (US)

(73) Assignee: Applied Sonics, Incorporated, Littleton, CO (US)

( * ) Notice: Subject to any disclaimer, the term of this patent is extended or adjusted under 35 U.S.C. 154(b) by 145 days.

(21) Appl. No.: 10/756,156

(22) Filed: Jan. 13, 2004

(65) Prior Publication Data

US 2004/0139792 A1 Jul. 22, 2004

Related U.S. Application Data

(60) Provisional application No. 60/441,468, filed on Jan. 21, 2003.

(51) Int. Cl.
G01N 29/32 (2006.01)

(52) U.S. Cl. ........................... 73/599; 73/602

(58) Field of Classification Search ................ 73/579, 73/599, 600

See application file for complete search history.

(56) References Cited

U.S. PATENT DOCUMENTS

| | | | |
|---|---|---|---|
| 3,779,070 A | 12/1973 | Cushman et al. | |
| 3,802,271 A * | 4/1974 | Bertelson | 73/865.5 |
| 4,412,451 A | 11/1983 | Uusitalo et al. | |
| 4,706,509 A | 11/1987 | Riebel | |
| 4,773,267 A | 9/1988 | Abts | |
| 4,852,396 A | 8/1989 | Tavlarides et al. | |
| 5,060,507 A | 10/1991 | Urmson et al. | |
| 5,121,629 A | 6/1992 | Alba | |
| 5,473,934 A | 12/1995 | Cobb | |
| 5,569,844 A | 10/1996 | Sowerby | |
| 5,623,095 A | 4/1997 | Beller | |
| 5,627,323 A | 5/1997 | Stern | |
| 5,629,485 A * | 5/1997 | Rose et al. | 73/599 |
| 5,767,407 A * | 6/1998 | Sinha | 73/579 |
| 6,029,507 A | 2/2000 | Faber et al. | |
| 6,109,098 A | 8/2000 | Dukhin et al. | |
| 6,295,873 B1 | 10/2001 | Condreva | |
| 6,401,538 B1 | 6/2002 | Han et al. | |
| 6,481,268 B1 | 11/2002 | Povey et al. | |
| 6,655,213 B1 * | 12/2003 | Reinhardt et al. | 73/597 |
| 6,935,164 B1 * | 8/2005 | Liljenberg et al. | 73/53.03 |

FOREIGN PATENT DOCUMENTS

JP  05126805 A  *  5/1993

(Continued)

OTHER PUBLICATIONS

Peters, F and Petit, L, A broad band spectroscopy method for ultrasound wave velocity and attenuation measurement in dispersive media, Ultrasonics, 2003, 357-363, 41.

(Continued)

Primary Examiner—Charles Garber
Assistant Examiner—Rose M. Miller
(74) Attorney, Agent, or Firm—Swanson & Bratschun LLC

(57) ABSTRACT

A method and apparatus for determining the composition of a containerized material, typically a suspension, through which ultrasonic waves are passed. The component ratios and particle sizes of a stationary or flowing material are determined by measuring ultrasonic wave phase and attenuation changes at multiple frequencies and deriving shape features from curves of the phase or attenuation versus frequency. Preferably, the frequency range employed extends below and above the frequency of maximum attenuation of the expected mean particle size in a suspension. The material composition is derived from analysis of the shape features of the derived curves.

21 Claims, 10 Drawing Sheets

FOREIGN PATENT DOCUMENTS

WO        WO 97/00436        1/1997

OTHER PUBLICATIONS

Coghill, P.J., M. J. Millen and B. D. Sowerby, On-line measurement of particle size in mineral slurries, Minerals Engineering, 2002, 83-90, 15.

Hipp, A.K., B. Walker, M. Mazzotti, and M. Morbidelli, In-situ monitoring of batch crystallization by ultrasound spectroscopy, Ind. Eng. Chem. Res. 2000, 783-389, 39.

Scott, D.M., A Boxman, C.E. Jochen, In-line particle characterization, Part. Part. Syst. Charact. 1998, 47-50, 15.

Coghill, P.J., M. J. Millen and B. D. Sowerby, On-line particle size analysis using ultrasonic velocity spectrometry, Part. Part. Syst. Charact. 1997, 116-121, 14.

Dukhin, A.S. and P.J. Goetz, Acoustic and electroacoustic spectroscopy, Langmuir 1996, 4336-4344, 12.

McClements, D.J., Principles of ultrasonic droplet size determination in emulsions, Langmuir, 1996, 3454-3461, 12.

Scott, D.M., A. Boxman, C.E. Jochen, Ultrasonic measurements of sub-micron particles, Part. Part. Syst. Charact. 1995, 269-273, 12.

Riebel, U., and F. Loffler, The fundamentals of particle size analysis by means of ultrasonic spectrometry, Part. Part. Syst. Characteristics, 1989, 135-143, 6.

Papadakis, E. P., Physical Acoustics, Principles and Methods, edited by W.P. Mason and R.N. Thurston, New York, Academic Press, 1976, v. 12, 277-374.

* cited by examiner

ULTRASONIC MONITOR OF MATERIAL COMPOSITION AND PARTICLE SIZE

RELATED APPLICATION DATA

This application claims benefit of Provisional Application Ser. No. 60/441,468, filed on Jan. 21, 2003, entitled ULTRASONIC MONITOR OF MATERIAL COMPOSITION.

TECHNICAL FIELD

The present invention relates to the measurement of material composition using non-contact ultrasonic waves. More specifically, the invention is an ultrasonic monitor for and method of determining the relative amounts of constituent components and the size of particles in a containerized material through which the ultrasonic waves pass.

BACKGROUND ART

There are many industrial applications which would benefit from quick, non-contact measurement of materials inside containers or flowing through pipes. Examples include emulsion preparation, separation processes, agglomeration reactors, milling operations and polymerization. For each of these applications there is a need for measurement of the constituent component ratios and contaminates, or characterization of physical properties such as particle sizes in slurries and emulsions. Similarly, for some applications, only the identity of the enclosed material (e.g., wax vs. oil) needs to be determined.

Various apparatus and methods for composition and particle size measurement utilizing ultrasound are known in the prior art. Several particle measurement systems described in the prior art make use of both attenuation and sound velocity measurements at a few selected ultrasonic frequencies. Sowerby, U.S. Pat. No. 5,569,844, describes a combination gamma ray and ultrasonic system that operates at two discrete frequencies to measure solids loading, particle size and solute concentration in a suspension. Both gamma ray measurements and the two-frequency velocity readings are used in a linear equation to calculate solute concentration in a stirred tank. Similarly, the particle sizes in preset ranges are found by using the two attenuation measurements, the velocity measurements and gamma ray density measurements in another linear equation. The two frequencies are selected to optimize measurement sensitivity for the expected particle distribution. Related International Application Number PCT/AU96/00362, Publication Number WO 97/00436, describes the combined use of gamma ray measurement and sound velocity at several discrete frequencies to measure particle size alone. Operation of a similar system developed by these inventors for mineral slurries is presented by P. J. Coghill et. al., Minerals Engineering, 15, 83–90 (2002). In addition, Reibel, U.S. Pat. No. 4,706,509, discloses a similar method featuring use of a plurality of discrete frequencies preferably selected based upon the range of anticipated particle sizes, and measures particle size concentration in the preset ranges by solving a set of linear equations formed from the measured attenuations.

Because of the significance of particle size to many industrial processes, far more patents are concerned with particle size measurements alone. Like the prior art noted above, Uusitalo, U.S. Pat. No. 4,412,451, and Cushman, U.S. Pat. No. 3,779,070, describe the use of attenuation at two discrete frequencies to monitor mean particle size and percent solids in a slurry. However, many other inventors have made use of multiple attenuation measurements covering a wide frequency range. To determine particle size distribution, these researchers have used size-dependent theories for attenuation and then compared these to actual measurements. These theories apply to very small particles where the attenuation is dominated by viscous and thermal effects. Relevant patents covering methods for size distribution based upon analysis of data points from a broad range of discrete frequencies are Dukhin, U.S. Pat. No. 6,109,098; Alba, U.S. Pat. No. 5,121,629; and Reibel, U.S. Pat. No. 4,706,509. The distributions are determined by assuming a starting particle distribution, predicting attenuation at each discrete frequency from the theory, comparing the predicted attenuations with actual attenuation measurements, adjusting the distribution and then repeating this procedure until a suitable match is achieved between prediction and measurement. This method has the disadvantage that a large number of physical properties of the particles and suspending medium must be known to make the predictions, especially for small particles (see McClements, D. J., Langmuir, 12, 3454–3461 (1996)) In addition, the numerical computations required to calculate the theoretical attenuations are very time consuming, and often unstable. These same disadvantages apply to the linear system inversion method of Reibel discussed above. Another complication is the lack of a suitable "multiple scattering" theory needed for dense slurries where the concentration exceeds about 5% volume concentration (see Riebel and Loffler, Part. Part. Syst. Charact. 6, 135–143, 1989). In addition, all of these theories assume spherical particles, and this is certainly not the case for most industrial slurries.

The use of ultrasonic velocity measurements for composition measurement alone is also well known. Such methods can be applied to suspensions and emulsions without concurrent measurement of particle size. Condreva, U.S. Pat. No. 6,295,873, describes a single-frequency transducer, "pulse-echo," method to detect a single contaminant added to a liquid sample held in a vessel. Changes in the transit-time of the ultrasonic waves are used to sense the presence of the contaminant without providing concentration measurements. Cobb, U.S. Pat. No. 5,473,934, describes a method and apparatus for monitoring the composition of a liquid/liquid or liquid/solid mixture flowing inside a process conduit. The above patent features the use of times of ultrasonic waves traveling through the clamp-on sensor mounts and conduit walls in conjunction with a calibration equation to provide component fractions of these binary mixtures. Urmson, U.S. Pat. No. 5,060,507, describes a different approach that relies on single-frequency resonances of a special chamber to provide composition measurement of a fluid sample. Tavlarides, U.S. Pat. No. 4,852,396 uses single-frequency sound velocity measurement to determine the ratios of two liquids contained in a reactor. Although sufficient for binary mixtures, none of these methods can provide composition information for three or more components. This is especially true when one of the components is a solid or liquid particle dispersed in one or more liquids.

Those skilled in the art readily understand the wide range of potential applications for composition and particle sizing measurement in various industries such as food, mining, pharmaceuticals, chemicals and petroleum. Product composition is an important indicator of quality for many industrial processes and must be monitored and controlled. The present invention is directed toward overcoming one or more of the problems discussed above.

SUMMARY OF THE INVENTION

The need in the art is addressed by a non-contact method of determining the composition of a material. The method consists of measuring the attenuation or phase of multiple ultrasonic waves transmitted through the subject material at multiple frequencies. From the measured attenuation or phase, an attenuation or phase curve is derived as a function of the change in the ultrasonic wave frequency. Shape features on the attenuation or phase curve can be identified which relate to the composition of the material thus a determination of the composition of the material can be made from an identified shape feature.

Typically, the material is a suspension in a container. The material may be flowing or stationary. The determination of the composition of the material may consist of many attributes including but not limited to a determination of the mean particle size of the particles in a suspension. Alternatively, the determination of the composition of the material may consist of a determination of a size range of the largest particles in a suspension. Alternatively, the determination of the composition may consist of a determination of a component ratio of various types of particles in a suspension. Alternatively, the determination of the composition of the material may consist of a determination of a component ratio among multiple suspending constituents in a suspension.

Preferably, the shape feature identified to determine mean particle size is the maximum slope of an attenuation curve where the wavenumber ka associated with the ultrasonic wave is approximately equal to 1. Similarly, the shape feature identified to determine the size range of the largest particles in a material suspension is preferably a width of the derivative of an attenuation curve near the frequency where ka≅1. In addition, the shape feature identified to determine a component ratio of the particles in a material suspension can be the maximum value of an attenuation curve near the frequency where ka≅1. Similarly, the shape feature identified to determine the component ratio of multiple suspending constituents in a material suspension can be a constant value taken from the phase curve at a frequency below the frequency where ka≅1. An alternative method of determining the component ratio of the particles in a material suspension is associated with a shape feature of a phase curve. In the alternative method, the component ratio is determined by the slope of the phase curve near the frequency where ka≅1.

The composition of a material may also be determined by comparison of a shape feature from an attenuation curve or phase curve with a known shape feature for a known material.

An alternative embodiment of the invention is an apparatus for determining the composition of a material. The apparatus consists of components, typically a single or pair of ultrasonic transducers, for measuring a wave attribute of multiple ultrasonic waves transmitted through a material at multiple frequencies. The wave attribute measured is typically the attenuation of the ultrasonic wave or the phase of the ultrasonic wave. In addition the apparatus consists of other components for deriving a curve from the measured wave attribute as a function of change in the ultrasonic wave frequency. The apparatus further consists of components for identifying a shape feature from the derived curve related to the composition of the material and thus determining the composition of the material by the shape feature. Preferably, the determination of the composition of the material from the shape feature proceeds according to the methods described above.

An alternative embodiment of the invention is an apparatus for determining the composition of a material in a container. The apparatus consists of a first ultrasonic transducer transmitting an ultrasonic wave into a material which is typically a suspension. The apparatus further consists of a second ultrasonic transducer receiving the transmitted ultrasonic wave from the material. The first ultrasonic transducer and the second ultrasonic transducer may transmit and receive the ultrasonic wave, respectively, at a select angle of offset relative to a line between the transducer centers. The first and second ultrasonic transducers may be shielded from the material by a protective wall.

All embodiments of the invention are applicable to dense suspensions of solid, liquid, or gas particles in a liquid or solid suspending material. As used herein, the term "particles" includes all such materials. Suspensions include, but are not limited to, slurries of solid particles or emulsions of liquids. All embodiments of the invention are also applicable to monitoring the composition of a mixture with or without the presence of particles. The invention may also be used to monitor the composition of a two-component suspending material in addition to particles, for example a dissolved solute in a second liquid with suspended solid particles. All embodiments of the invention are applicable to stationary or flowing materials.

BRIEF DESCRIPTION OF THE DRAWINGS

The present invention can be more readily understood in conjunction with the accompanying drawings, in which.

DETAILED DESCRIPTION OF THE PREFERRED EMBODIMENT

Figure 1:
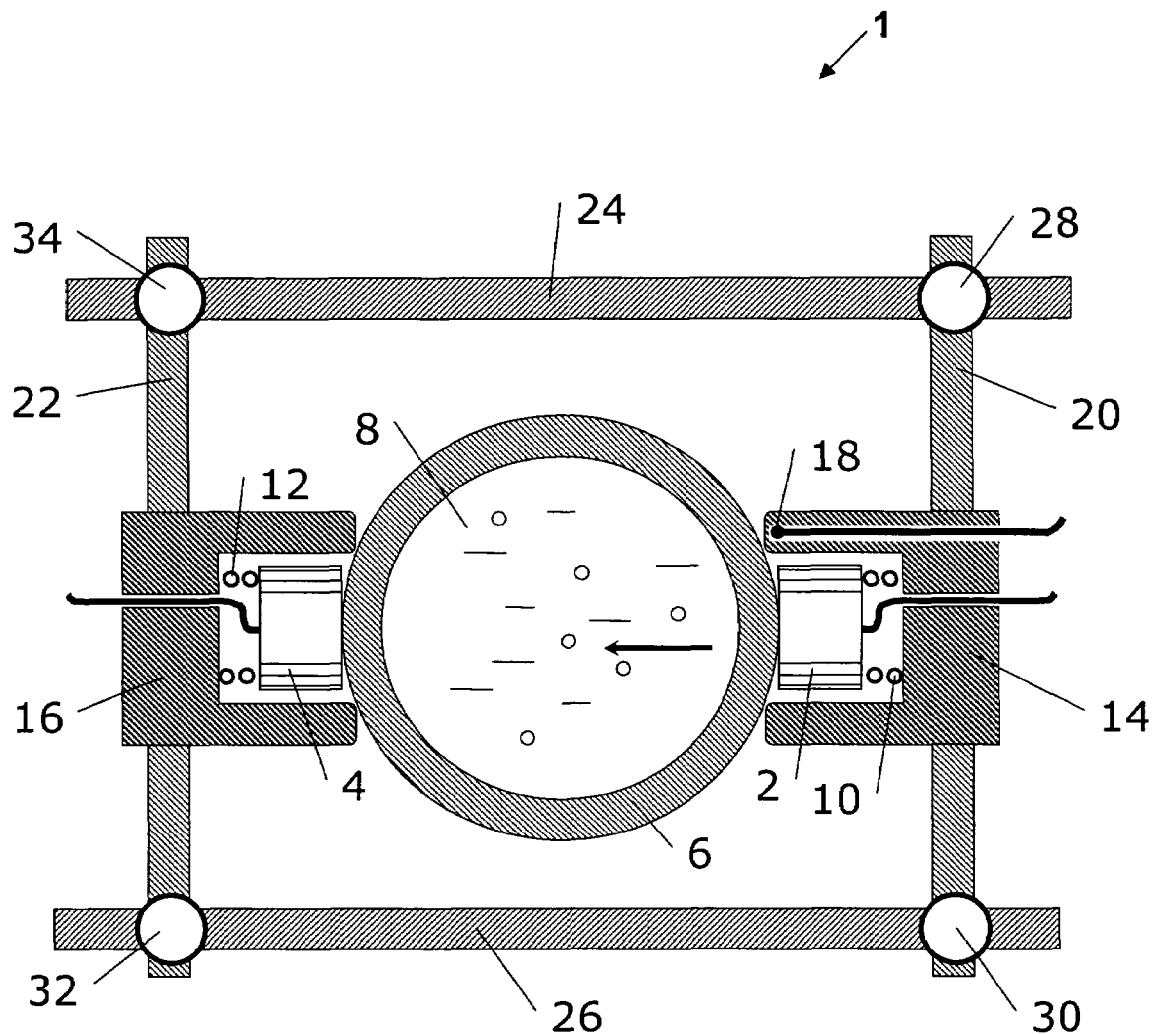
FIG. 1 is a plan view of a first embodiment of the invention for monitoring materials inside a container such as a pipe carrying a fluid.

FIG. 1 shows a plan view of a first embodiment of an ultrasonic monitor 1 featuring two ultrasonic transducer assembles 2 and 4 mounted on the outside of a conduit or container 6 holding material 8. Although material 8 is depicted as being located in a conduit 6 in FIG. 1, the material 8 may be located in any type of pipe, container, or vessel. The material 8 as used throughout this application is defined as a suspension of solid, liquid, or gas particles in a liquid or other solid-suspending material. Typically, a material 8 will be a slurry of solid particles or an emulsion of liquids, however, Applicant's invention is not limited to these two representative suspensions. The two ultrasonic transducer assemblies 2, 4 are clamped to the outside of the conduit 6, such that ultrasonic waves may pass through the conduit 6 walls. The ultrasonic transducers 2, 4 provide for both the generation and transmission of ultrasonic waves and the reception of ultrasonic waves. Although a cylindrical conduit 6 is illustrated, the conduit 6 (or other container) can have any shape (e.g., square, spherical, etc.). However, in the embodiment shown in FIG. 1, the surfaces of the container must allow the ultrasonic transducers 2, 4 to be mounted on the outside, and the ultrasonic waves to be coupled to the walls. The springs 10 and 12 inside the mounting blocks 14 and 16 force the two ultrasonic transducers 2, 4 against the conduit 6 wall. Before mounting the ultrasonic transducers 2, 4, a small amount of coupling grease may be applied to the transducer faces to facilitate conduction of the waves into the container walls. In addition to the ultrasonic transducers 2, 4, a temperature probe 18 is mounted inside the mounting block 14. The temperature probe 18 is positioned close to the conduit 6 to monitor the temperature of the conduit 6 walls and material 8 inside. Thermally conductive compound may be applied to maximize heat transfer from the conduit 6 to the temperature probe 18.

Clamping bars 20 and 22 run through the mounting blocks 14, 16, respectively, to provide clamping force against the conduit 6. Perpendicular clamping bars 24 and 26 run through clamping bars 20, 22 forming a rectangle and are held in place by thumbscrews 28, 30, 32, 34. The entire clamping assembly is mounted to the conduit 6 by first tightening screws 28, 30, 32 as the assembly is held against the conduit 6. Forcing clamping bar 22 towards clamping bar 20 and tightening screw 34 then locks the assembly in place. The design of the clamping assembly depicted in FIG. 1 forces the two ultrasonic transducers 2, 4 to be aligned with each other on opposite sides of the conduit 6. Proper alignment maximizes the reception strength of ultrasonic waves transmitted between the transducers.

Since wave velocity measurements are sensitive to temperature, the temperature of the contained material 8 is measured to allow correction of the determination of material composition for temperature changes. For containers that are good heat conductors, the walls will be near thermal equilibrium with the contained material 8, and an external temperature probe 18 can be used to monitor material temperature. As shown in FIG. 1, the external temperature probe 18 can be clamped to the wall of the container. If required, the temperature sensor and a portion of the container can be covered with insulation to reduce the effects of external heating or cooling.

Figure 2:
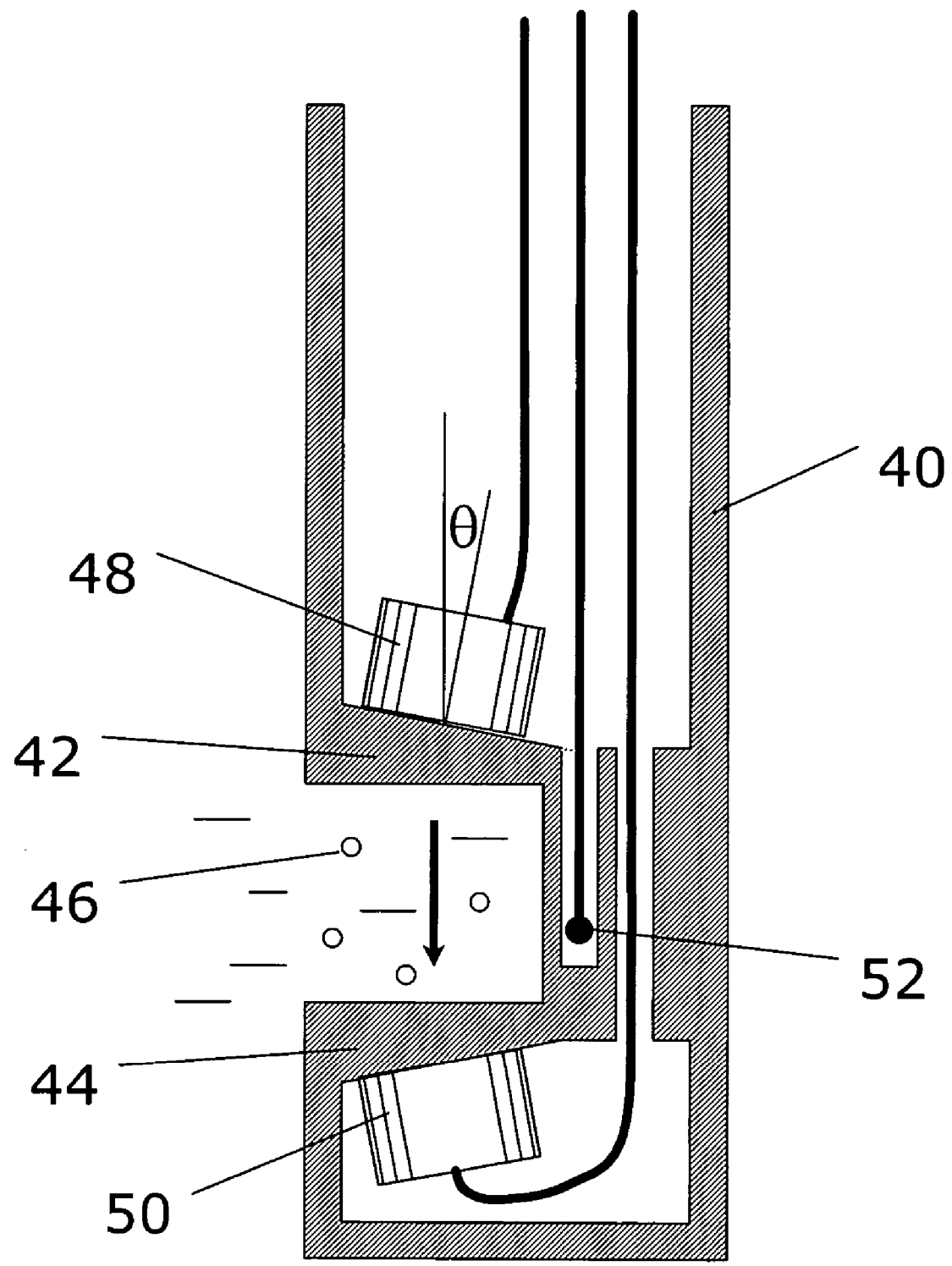
FIG. 2 is an elevation view of a second embodiment of the invention where the transducers are enclosed within a probe that is inserted into the material.

FIG. 2 shows another embodiment of the invention where ultrasonic transducers 48, 50 are enclosed within a probe 40 which can be inserted into a fluid material 46. The probe 40 can be immersed into a mixing vessel or inserted into a flow line though a flanged port or swagged fitting. In use, ultrasonic waves pass through the probe walls 42, 44 and the material 46 contained between. The non-contact ultrasonic transducers 48, 50 are thus shielded from any potentially corrosive or hazardous material. A temperature probe 52 may be placed within the probe 40 as close as possible to the material 46. In this way, the temperature probe 52 is most likely to be in thermal equilibrium with the material 46.

Figure 3:
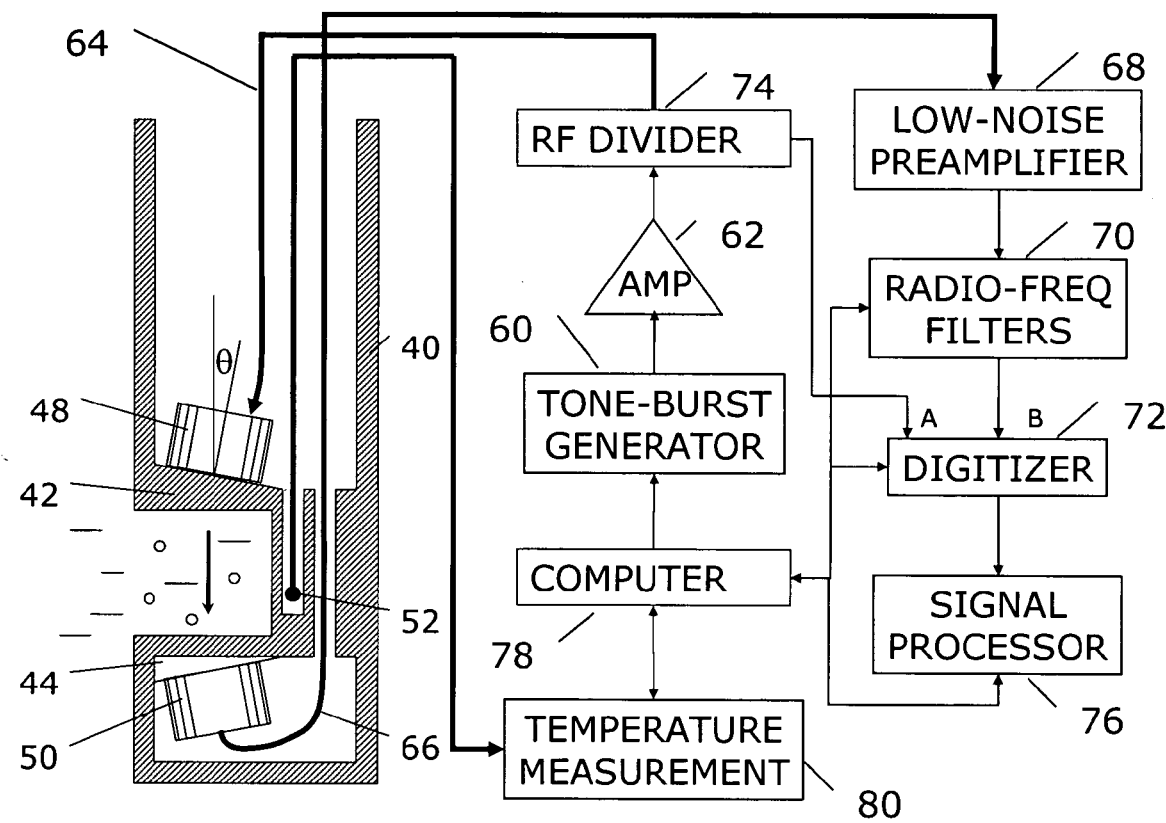
FIG. 3 is a block diagram of the electronic system used in this invention.

The electronics system illustrated in FIG. 3 is used to excite and receive ultrasonic waves, compute ultrasonic property values and, as described in detail below, provide component concentrations, particle measurements and other composition data. Although shown associated with the embodiment of FIG. 2, the same electronics configuration may be used with the FIG. 1 or other sensor embodiments. Tone-burst generator 60, which may be a commercially available product such as a Hewlett Packard 3314 tone burst generator, produces a voltage burst consisting of several sinusoid cycles at a selected frequency. The amplifier 62, which may be a commercially available product such as an Amplifier Research 150A250 amplifier, boosts the burst to a high voltage suitable for driving piezoelectric ultrasonic transducers 48, 50 (e.g. 300 volts). The transducers 48, 50 can be used for either transmitting or receiving an ultrasonic wave. In the FIG. 2 embodiment, the high-voltage burst is applied to transducer 48 through radio frequency (RF) cable 64 causing transmission of an ultrasonic wave through wall 42. Transducer 50 converts the ultrasonic wave traveling though the measurement gap into an electrical signal that is carried to the low-noise preamp 68, which may be a commercially available product such as an Analog Devices 321A pre-amp, by RF cable 66. Both transducers 48, 50 may be commercially available contact-inspection devices such as Staveley NDT transducers, preferably with a center frequency of 5 MHz. In order to operate over a wide frequency range (e.g., 0.1 to 20 MHz) the piezoelectric elements of the transducers 48, 50 must have high mechanical damping and be electrically un-tuned. Alternate embodiments of the invention could utilize additional transducers and multiplexors to cover a wider or different frequency range if needed.

The preamplified received signal is input to a set of radio frequency filters 70. These analog filters remove frequencies in the signal that are outside the frequency of the tone-burst. In particular, since the transducers 48, 50 of a preferred embodiment have the greatest natural response near 5 MHZ, some energy at this frequency is almost always present in the received signal, even though the tone burst frequency may be much lower (e.g., 0.1 MHz). The radio frequency filters remove the un-wanted frequency components prior to digital conversion by digitizer 72 which may be a commercially available product such as a Gage Instruments CompuScope 250.

Prior to application to the transmitting transducer 48, the tone-burst signal is passed though resistance divider 74 to provide a signal level suitable for digital conversion. Both this input signal and the filtered received signal are converted using a two-channel digitizer 72 preferably operating at 50 MHz. To allow for later phase measurement, the digitizer 72 must maintain the same timing relationship between the digitized samples of both signals. The digitized signal samples are input into a signal processor 76 for rapid analysis of the two signals. The signal processor 76 calculates the frequency spectrum of the transmitted and received signals. This processing can be done with separate dedicated signal processing hardware or alternatively on a microcomputer 78. The microcomputer 78 may also control the tone-burst frequency, signal filtering, digitization and processing.

Since phase measurements are sensitive to temperature changes, the material temperature is measured to ensure accurate results. The temperature measurements allow correction of the determination of material composition for temperature variations. To provide a complete non-contact measurement system, the temperature probe 52 may be contained inside the clamp or probe body as shown in FIG. 2. Similarly, the temperature probe 18 of the FIG. 1 embodiment may be contained in mounting block 14. Temperature monitoring electronics 80 as shown in FIG. 3 conditions and reads the temperature from the probe and communicates the reading to microcomputer 78.

Although the embodiments of the invention shown in FIG. 1 and FIG. 2 are described as using a transducer and separate receiver for thru-transmission, it is possible to implement the invention using a pulse-echo configuration with only one transducer. In the pulse echo embodiment, a tone burst is emitted, the system waits and an echo is received from the inside wall of the container. This echo is then analyzed in the same manner as a thru-transmission signal.

To determine the components of the material in the container, measurements of the signal phase and attenuation are made using the apparatus of FIG. 3. Many available methods for phase and attenuation measurement use signals of one primary frequency. The present invention uses a multi-frequency approach that is more accurate and provides particle size and composition measurement on suspensions. First, a low frequency is selected which is well below the expected frequency for maximum attenuation by the particles. Phase and attenuation measurements are made at this first frequency using the methods described below. The emitting frequency is then increased for the next step and the measurements repeated until the desired frequency band is covered. For example, 44 frequencies can be selected between 0.1 and 20 MHz in logarithmic steps. For each step, multiple phase and attenuation measurements can be taken and averaged to smooth out signal variations due to noise and scattering changes. The ultrasonic transducers 48, 50 of FIG. 2 must have adequate sensitivity at each of the frequency steps to generate and receive sufficient ultrasonic energy.

Conventional methods for measuring the ultrasonic phase (or velocity), such as the pulse-echo overlap method (see E. P. Papadakis, Physical Acoustics, Principles and Methods, vol. XII, pp. 277–374, 1976), cross-correlation method and other time-domain measurements do not provide the precision required to determine the composition of materials. Therefore, in the present invention, the entire received pulse is transformed to the frequency domain and the change in phase for different compositions is measured. The required accuracy of the phase differences may be obtained with a Discrete Fourier Transform, which can be viewed as a Least Squares fit of the appropriate sine wave to the entire tone burst. The phase angle of the resulting spectrum is calculated at the specific frequency of the emitted tone burst (e.g. 5.0 MHz). However, this phase can jump between $-\pi$ and $\pi$ as the frequency increases and must first be "unwrapped" as described by Peters, F. and Petit, L., Ultrasonics, 41, 357–363, (2003).

As shown in FIG. 2 and FIG. 3, the transducers 2, 4 (FIG. 2); 48, 50 (FIG. 3) are protected by locating them behind walls of a material that will not be damaged by the potentially corrosive or hazardous material to be monitored. If these walls are sufficiently thick, the device can meet electrical safety standards for use in explosive environments. However, ultrasonic wave reflections within these walls may interfere with the reception of the transmitted tone-burst wave. The multiple-reflected echoes within each wall add to the direct wave reaching the receiver.

Figure 4A:
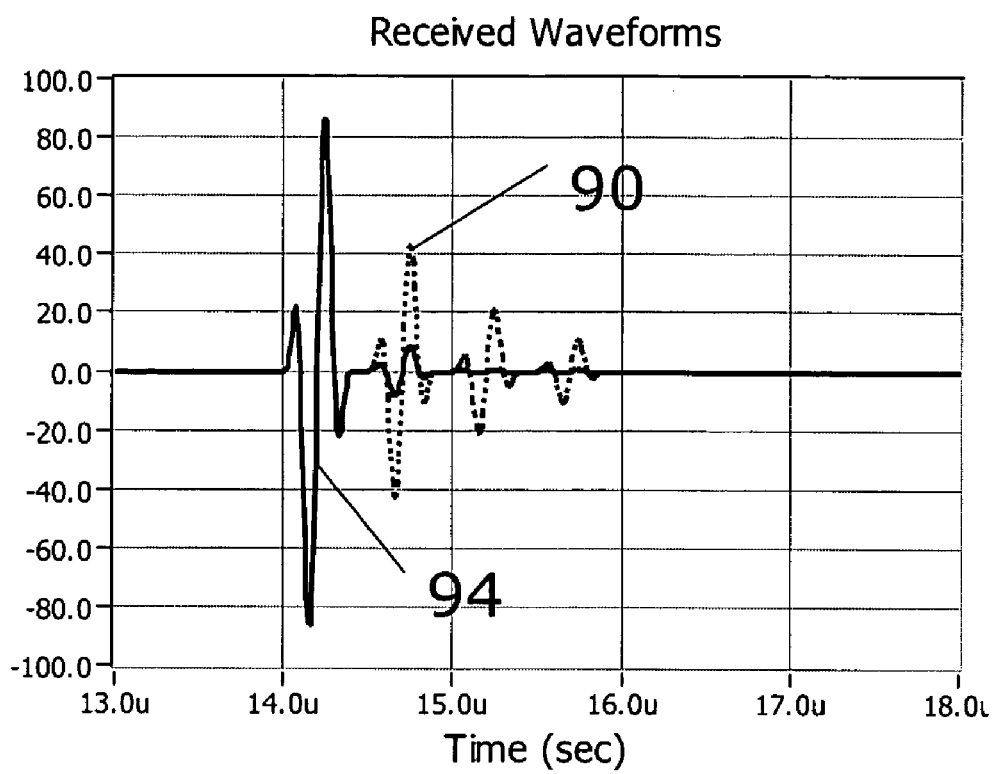
FIG. 4(a) is a plot of a simulation of direct waves and multiple echoes traveling through the apparatus of the FIG. 2 embodiment of this invention.
Figure 4B:
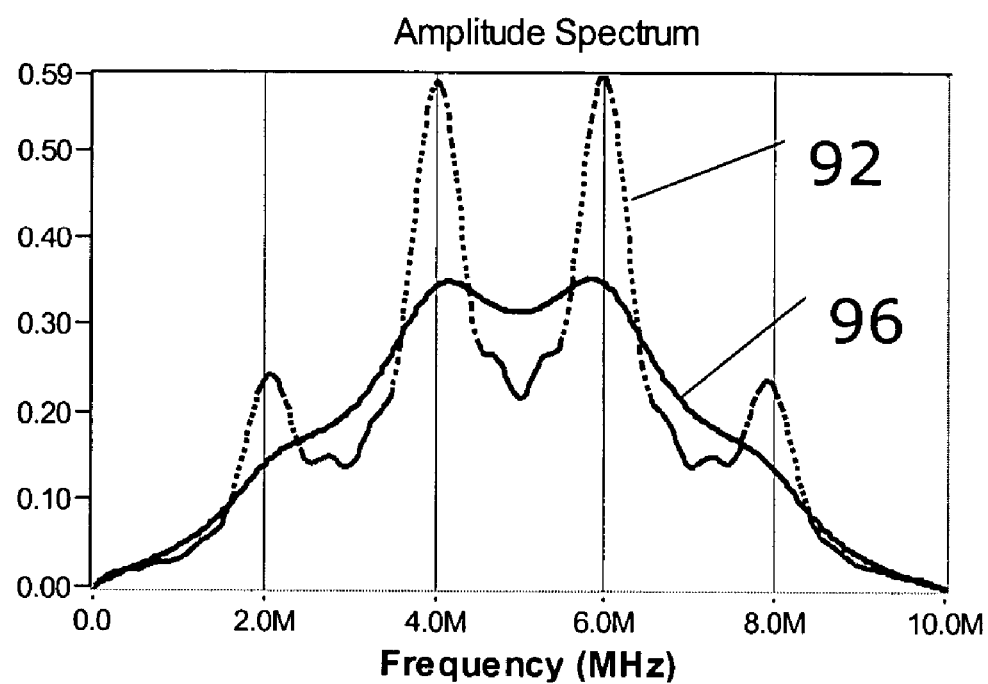
FIG. 4(b) is a plot of the resulting frequency spectrum of a simulation of direct waves and multiple echoes traveling through the apparatus of the FIG. 2 embodiment of this invention.

FIG. 4 illustrates this interference showing a simulation of a short-duration tone-burst traveling through two 9.5 mm thick aluminum walls separated by a 22 mm water path. FIG. 4a shows the received time waveforms and FIG. 4b shows the calculated frequency spectrum for the 5 MHz center-frequency burst. Waveform 90 is the direct wave received by the receiving transducer and shows the multiple echoes within the aluminum walls. A short burst is used for the simulation because it more clearly shows the multiple echoes. The resulting frequency spectrum 92 is shown in FIG. 4b. This spectrum has large peaks and nulls due to the presence of the multiple echoes. The shape of the received spectrum is clearly distorted compared to the broad, smooth spectrum of the burst signal without the echoes. This distortion complicates the measurement of true attenuation and phase spectrum-shapes as require to implement the invention.

To minimize the interference of the multiple echoes for apparatus with thick walls, preferably, both transducers may be tilted with respect to the centerline between them. As illustrated in FIG. 2, the walls are tapered at angle $\Theta$ to provide this tilt. In this configuration, the multiple echoes dissipate quickly within the wedge shaped walls, yet the direct wave travels just through the gap. The tilt angle $\Theta$ for best direct-wave transmission can be computed using Snell's law and estimated sound velocities of the materials. Waveform 94 shows the significant reduction in echo amplitudes when the walls are tilted at an angle of 4 degrees. Nevertheless, there is little reduction in direct wave amplitude. The tilt results in a much smoother frequency spectrum 96 more suitable for the spectrum-shape measurements used in this invention.

Description of Particle Size Measurement

Preferably, the frequency dependent attenuation is calculated from the magnitude of the calculated spectrum at each emitted frequency. Following Peters, F. and Petit, L., Ultrasonics 41, 357–363 (2003), the attenuation coefficient $\alpha(f)$ can be expressed as:

$$\alpha(f) = -\frac{\log[A_R(f)/A_T(f)]}{D_T} \quad [1]$$

where $A_R(f)$ is the magnitude of the received signal spectrum at frequency f, and $A_T(f)$ is the magnitude of the transmitted signal spectrum. $D_T$ is the total distance in the materials over which the attenuation takes place. For a suspension, the excess attenuation is the attenuation coefficient with particles minus that for the suspending material alone.

Figure 5:
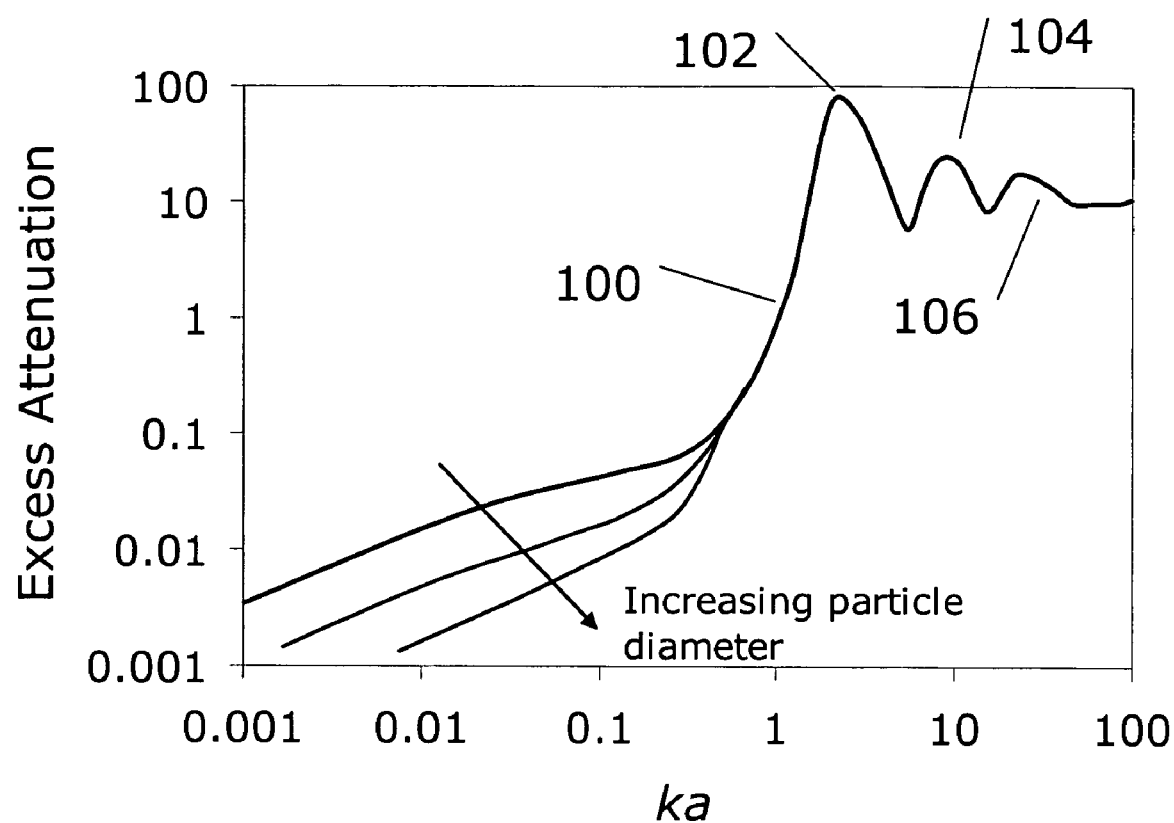
FIG. 5 is a generalized plot of frequency-dependent attenuation of ultrasonic waves in a suspension versus dimensionless wavenumber ka.

FIG. 5 illustrates the typical frequency dependence of the attenuation for low concentrations of spherical particles with radius a suspended in a fluid. The excess attenuation is plotted against the dimensionless wavenumber ka where $k=2\pi/\lambda$ and $\lambda$ is the wavelength. For small wavenumbers (ka<<1) the attenuation is dominated by viscous and thermal losses and is dependent on the particle radius. For ka>>1 attenuation is primarily due to scattering of energy by the particle and the curve is independent of particle radius. The attenuation curve typically has sharp rise 100 near ka≅1, followed by a primary peak 102 and several smaller peaks 104 and 106 at frequencies characteristic of resonances within the particles.

Figure 6:
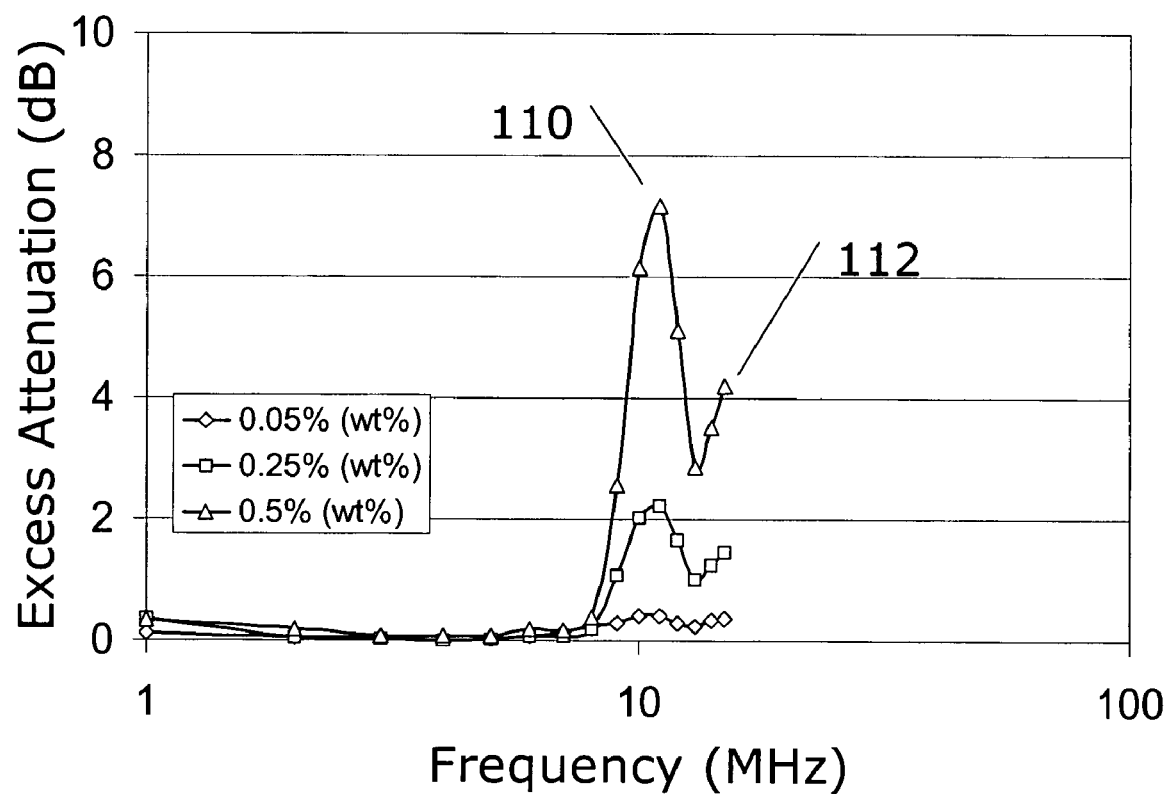
FIG. 6 is a plot of multi-frequency attenuation data measured for a dispersion of 65 μm diameter polystyrene particles in distilled water.

FIG. 6 illustrates the frequency dependence of the attenuation for particles of the same size in suspensions of various concentrations. FIG. 6 shows a plot of measured excess attention for 65 μm diameter polystyrene particles in distilled water (standard deviation 10 μm). The measurements were made using wide bandwidth 10 MHz, 6.4 mm dia. transducers in the probe configuration of the embodiment shown in FIG. 2. The transducers 48, 50 were shielded behind a ⅛" thick wall of stainless steel and the gap containing the mixture 46 had a 2.54 cm separation. As shown in FIG. 6, the excess attenuation for this monodisperse suspension has a single peak near 10 MHz that is characteristic of the mean particle size. Note that the abrupt rise in the curve and the peak 110 near ka≅1 remain constant as the particle concentration increases. The start of a secondary scattering peak 112 can be seen at frequencies near 15 MHz.

When particles of various sizes are present, the attenuation curve becomes the weighted average of the curves for each size. The attenuation peaks for the particles with the highest concentration will contribute the most to the average attenuation curve. However, it has been found that for typical suspensions, the averaged attenuation curve has a distinct, abrupt rise in attenuation that occurs near the frequency for which $ka_m \cong 1$, where am is the mean particle diameter. As the mean particle size increases, this abrupt rise shifts to lower frequency. Measurement of this rise forms the basis of the particle measurement method of this invention.

Figure 7:
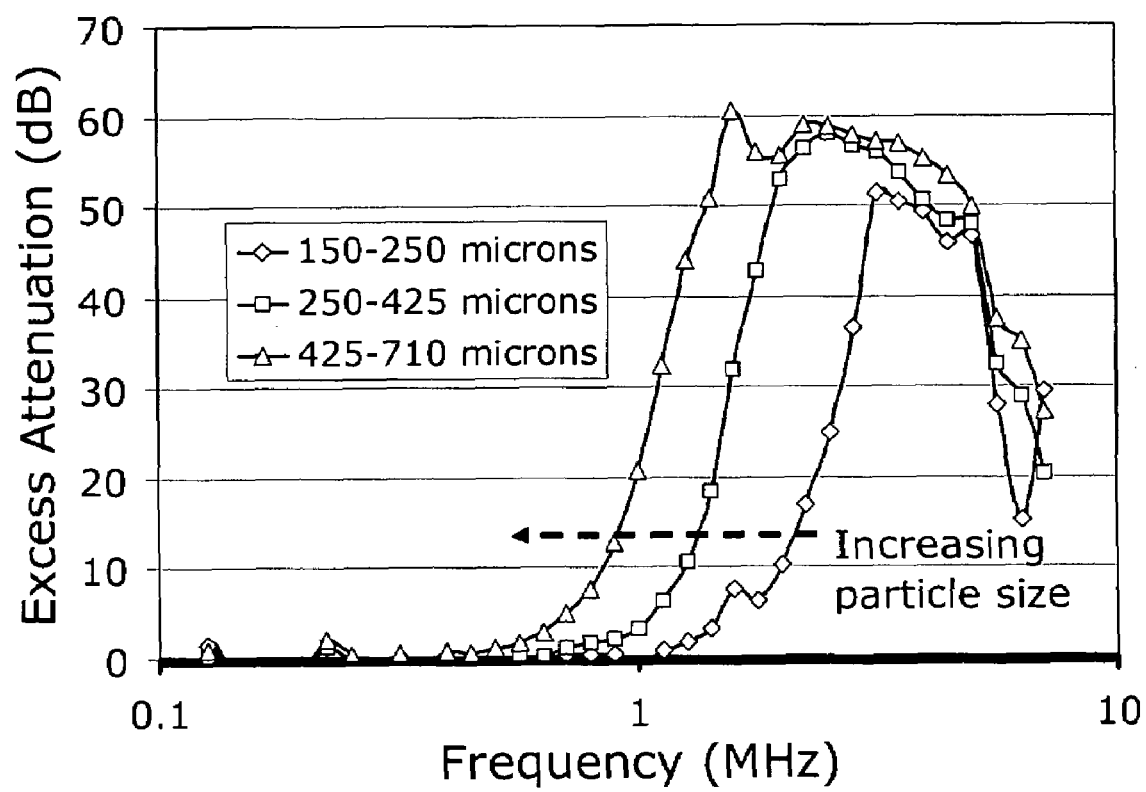
FIG. 7 is a plot of the attenuation curves for three slurries containing 10 weight percent wheat particles in a food oil.

To illustrate how particle size is determined, FIG. 7 illustrates the abrupt rise in the attenuation curve for a food slurry containing wheat particles in an oil. Attenuation curves measured with the apparatus of FIG. 3 are shown for three slurries prepared from particles sieved into the three size ranges indicated. These particles are very non-spherical, and have a wide range of sizes within the sieve bins indicated. As expected, the abrupt rise in attenuation moves to lower frequencies for larger particles. These curves do not show sharp resonance peaks for high frequencies because these are averaged out for the many particle sizes.

Figure 8:
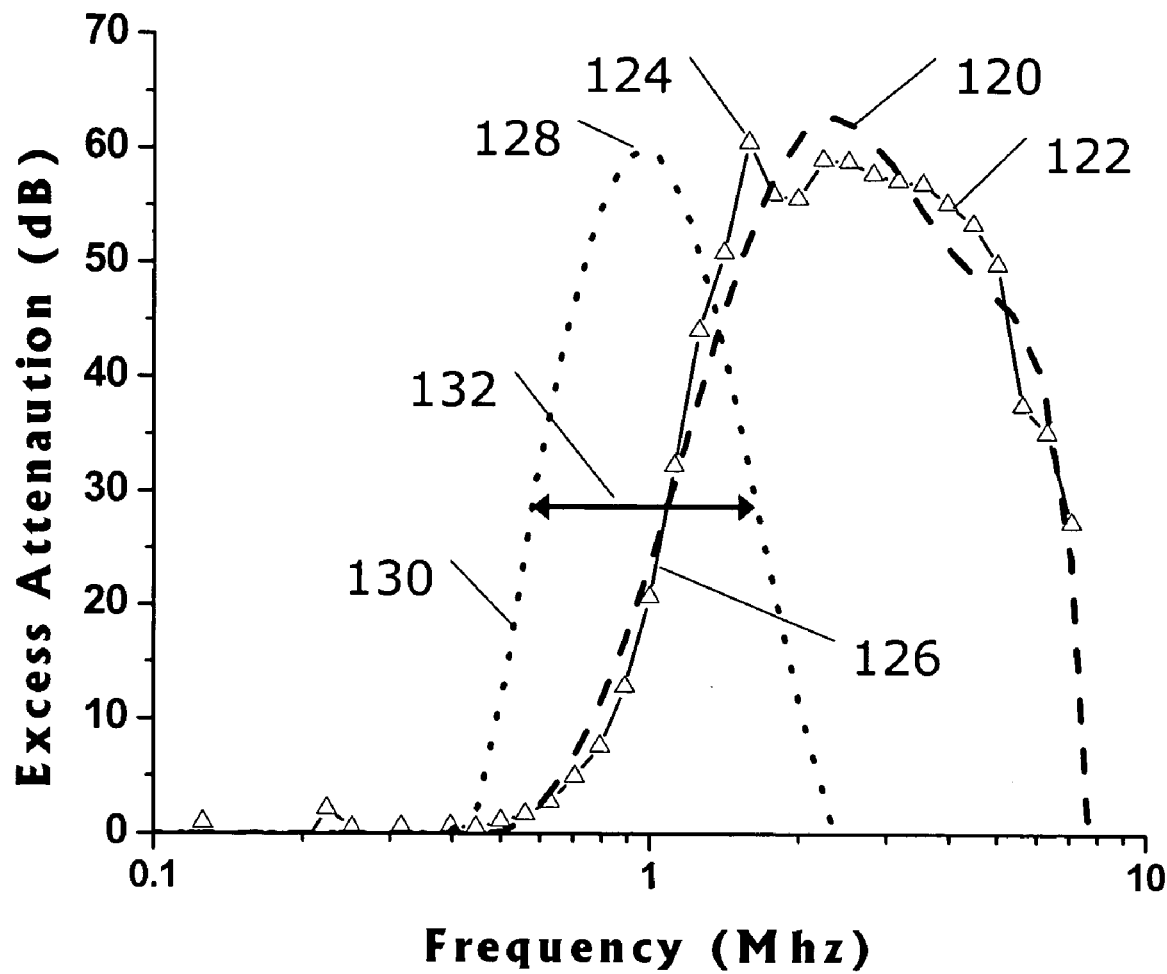
FIG. 8 is a plot illustrating how the shape features are calculated from the attenuation curve of a wheat particle slurry.

The present invention uses an analysis of the shape of the attenuation curve to determine three characteristics of the slurry; the mean particle size of the slurry, the size range for the largest particles and the component ratio of the particles. The mean size is calculated by first fitting a polynomial curve to the excess attenuation measurements. To provide a good fit to the rapidly increasing attenuation curve, a polynomial fit order of 6 to 9 may be required. Fitting reduces the effects of small variations in the attenuation near the peak due to secondary resonances and the echo interference discussed above. FIG. 8 shows an 8th order fit 120 to the attenuation curve 122 of the largest-particle slurry of FIG. 7. Note that a small peak 124 caused by the echo interference is smoothed by the polynomial curve fitting. The mean particle size is determined from the point of maximum slope in the abrupt rise 126 in the attenuation curve. In a preferred embodiment, this point of maximum slope $F_p$ is calculated as the frequency for which a peak 128 occurs in the derivative 130 of the fit. As the particle size increases or decreases in the suspension, this frequency can be used to monitor changes in the mean particle size.

In addition to particle size information, the shape of the attenuation curve also provides information on the size range of the larger particles. It has been found that the slope of the rise changes with the size range of the larger particles. This is illustrated by comparing the slopes for the uniform sized particles in FIG. 6 with the particles of various sizes shown in FIG. 7. The slope of the curve decreases as the particle size range increases. In a preferred embodiment of the invention, the change in slope is monitored by calculating the half-amplitude width 132 of the peak in the derivative as shown in FIG. 8. The half-width $W_p$ increases as the particle size range increases.

Also as illustrated on FIG. 6 the maximum attenuation value increases as the particle concentration increases. In a preferred embodiment of the invention, the maximum value of the excess attenuation curve $\alpha_M$ is used as a shape feature to monitor particle fraction $\phi_p$.

Once the shape features of the attenuation curve are determined, these values are used in a calibration equation to provide the mean particle diameter am and the size range Δa of the largest particles. In a preferred embodiment, the calibration equations have the following quadratic forms $$a_m = A_a + B_a * F_p + C_a * F_p^2 \text{ and} \quad [2]$$

$$\Delta a = A_{\Delta a} + B_{\Delta a} * W_p + C_{\Delta a} * W_p^2 \text{ and} \quad [3]$$

$$\phi_p = A_{\phi p} + B_{\phi p} * \alpha_M + C_{\phi p} * \alpha_M^2 \quad [4]$$

where A#, B#, C# are calibration coefficients of the respective equation as marked by subscript #.

To calibrate the apparatus of the invention, the coefficients $A_a$, $B_a$, and $C_a$ are determined by regression of known particle mean-diameter readings with measurements of the frequency $F_p$. The coefficients $A_{\phi p}$, $B_{\phi p}$, and $C_{\phi p}$ are determined by regression of known particle fraction readings with measurements of the maximum attenuation feature $\alpha_M$. Similarly $A_{\Delta a}$, $B_{\Delta a}$, and $C_{\Delta a}$ are determined by regression of known particle size-range readings with measurements of the derivative peak $W_p$. The known particle size or concentration readings are determined by independent analytical means on samples of the measured materials taken in the laboratory or while the apparatus is on-line. The calibration measurements for the regressions are recorded from the apparatus for the sample being monitored.

The particle size monitoring method of this invention has the advantage that no attenuation theory is required for inverting the particle distribution. In addition, since the mean particle size and particle size range are calibrated using samples of the actual suspension, no additional physical property information is needed. The invention makes use of only the region of the attenuation curve where the slope of the curve increases abruptly corresponding to ka≅1. Thus the required attenuation measurements can be made over a smaller frequency range than prior art methods. Thus, the frequency measurements are simplified and allow the use of available commercial transducers.

Description of Material Composition Measurement

To provide the composition measurements of this invention, the frequency dependent, "excess phase" is calculated from the phase spectrum of the received pulse at each emitted frequency. Following Peters, F. and Petit, L., Ultrasonics, 41, 357–363 (2003), the velocity of sound $c_T(f)$ in the material between the sensors can be expressed as a function of the phase:

$$c_m(f) = -\frac{2\pi \times f \times D_m}{\varphi_m(f)} \quad [5]$$

where $\phi_m(f)$ is the phase shift of the received signal spectrum at frequency f as it travels though a distance $D_m$ of the material. Like the excess attenuation, the excess phase $\phi_e(f)$ is the measured phase with all material components minus that for a reference material alone:

$$\phi_e(f)=\phi(f)_{[mixture]}-\phi(f)_{[reference]} \quad [6]$$

The reference material can be the primary liquid in a mixture, or the suspending fluid for a slurry. For many liquid and solids materials, c(f) is relatively constant over the frequency range where attenuation is low. Thus, from equation 5, the excess phase divided by frequency $\phi_e(f)/f$ will be a constant when the velocity is constant. This parameter is the key to the measurement of the composition of the materials and is referred to herein as the "normalized phase". The normalized phase varies with frequency when absorptive materials are added to the liquid. This variation is used to monitor the amounts of suspended components.

Figure 9:
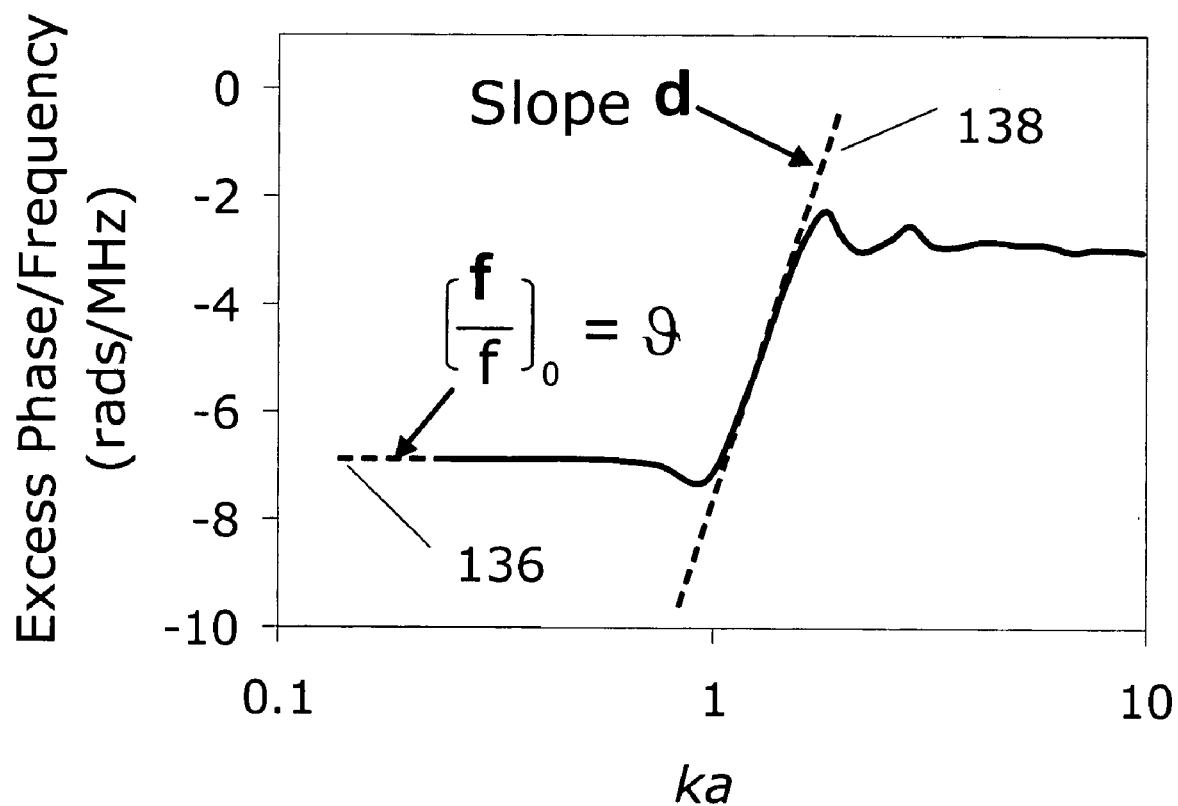
FIG. 9 is a generalized plot of frequency-dependent phase in a suspension versus dimensionless wavenumber ka. This figure illustrates how shape features are calculated from the phase curve.

FIG. 9 illustrates the frequency dependence of the phase for particles with radius a suspended in a fluid. The excess phase is plotted against the dimensionless wavenumber ka. For small wavenumbers (ka<<1) the normalized phase is the constant value $\phi_e(f)/f$ as described above. For simplicity in the following equations, this normalized phase value is termed $\vartheta$. For ka>1 the phase varies with frequency because of wave scattering and attenuation by the particles. However, the phase curve has a predominantly linear shape for frequencies below ka≅1 to several ka. Comparison with FIG. 5 shows that this range corresponds to that of the sharp rise 100 in attenuation caused by scattering.

The present invention uses the shape of the normalized phase curve to provide the component ratios for the material composition. Both the constant phase for ka<1, and the slope of the phase curve near ka≅1 are used. The constant values are determined by fitting a horizontal line 136 to the measured phase data below ka≅1. As described below, these values are used to calculate the component ratios $\phi_1$ and $\phi_2$ of the materials that suspend the particles. The component fraction $\phi_p$ of the particles is calculated from the slope $\delta$ of the phase curve. It has been found that the slope increases as particle concentration increases. The slope is determined by first fitting a line 138 to the curve generated from excess phase measurements. In a preferred embodiment, the fit is taken over a frequency range of width $W_p$ centered about $F_p$. As is the case with the attenuation analysis discussed above, curve fitting reduces the effects of small variations in the curve near $F_p$ due to secondary resonances and echo interference. Note that $\phi_p$ can be monitored either from the slope of this line or from equation 4 above or both. In practice, it has been found that $\phi_p$ from equation 4 is more stable for dense suspensions.

Figure 10:
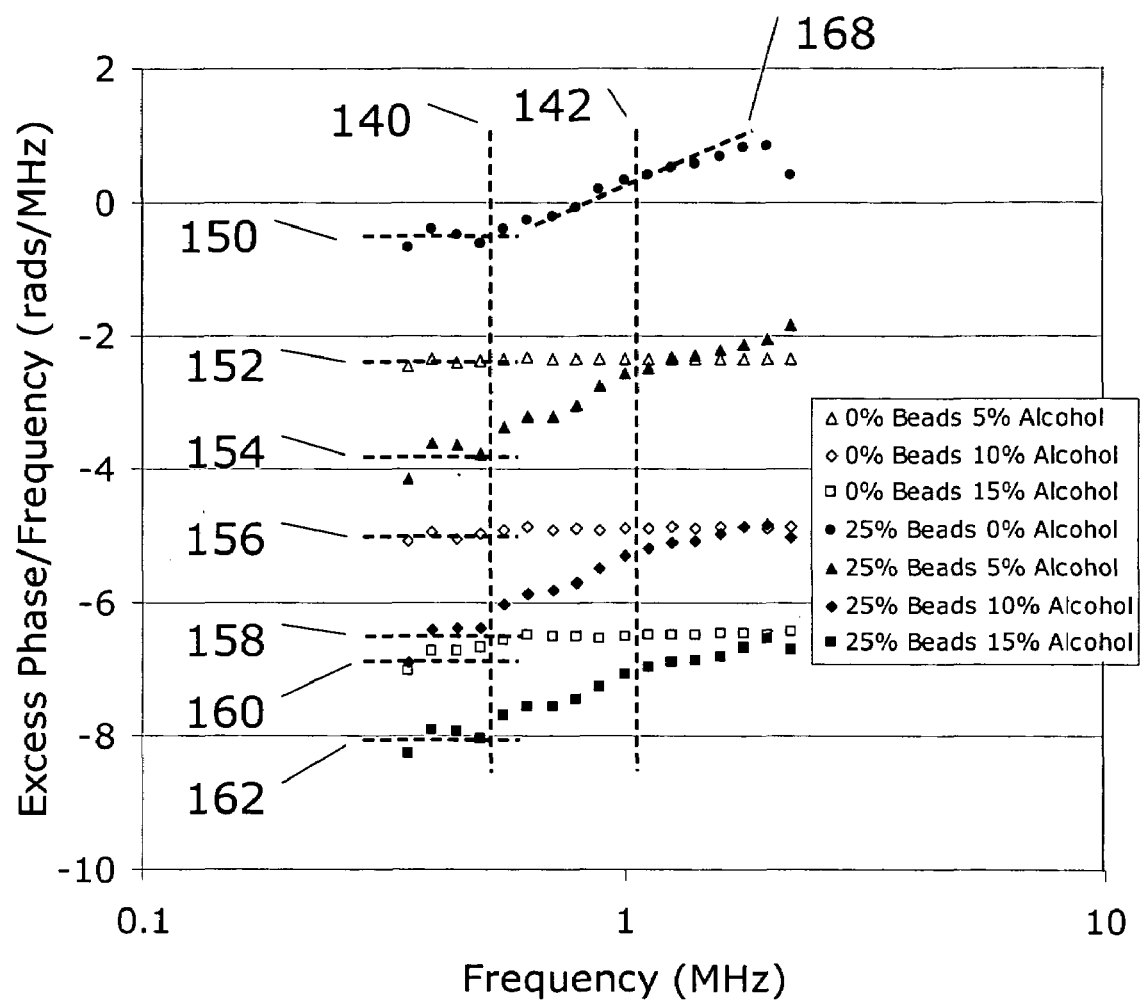
FIG. 10 is a plot of example measurements of frequency-dependent phase in a three-component slurry of water, ethyl alcohol and glass particles.

FIG. 10 shows a plot of the measured phase for mixtures of various concentrations of 500 μm mean-diameter glass beads in distilled water and ethyl alcohol, illustrating the frequency dependence of the normalized phase for a slurry. The left vertical line 140 in FIG. 10 corresponds to the frequency $F_c$ below ka=1 where the excess attenuation begins to rise with frequency (see FIG. 6 as an example). This frequency can be found by any number of methods known to those skilled in the art. For example, a threshold level can be placed on the excess attenuation data, and $F_c$ found as the lowest frequency where the attenuation exceeds this threshold. The normalized phase is almost constant below this frequency, and the value is estimated as the level of a horizontal line fitted to the data below $F_c$. These constant phase values are indicated as features 150, 154, 156, 158, 160, 162 of FIG. 10 for different glass bead and alcohol ratios. The right vertical line 142 of FIG. 10 corresponds to the point of maximum slope $F_p$ in the excess attenuation curve discussed above (element 128 of FIG. 8). A straight line 168 may be fitted to the measured phase points that are within $W_p/2$ of this line. The slope of line, $\delta$, is calculated from this fit and used to determine the particle fraction measurements.

Once the shape features of the normalized phase curve are determined, these values are used in a calibration equation to provide the component ratios $\phi_1$, $\phi_2$ and particle fraction $\phi_p$. In a preferred embodiment, these calibration equations have the following forms $$\phi_p = A_{\phi p} + B_{\phi p}*\delta \text{ and} \quad [7]$$

$$\phi_1 = A_{\phi 1} + B_{\phi 1}*\vartheta + C_{\phi 1}*\vartheta^2 + D_{\phi 1}*\phi_p + E_{\phi 1}*T \text{ and} \quad [8]$$

$$\phi_2 = A_{\phi 2} + B_{\phi 2}*\vartheta + C_{\phi 2}*\vartheta^2 + D_{\phi 2}*\phi_p + E_{\phi 2}*T \quad [9]$$

where A#, B#, C#, D# and E# are calibration coefficients of the respective equation as marked by subscript #. In these calibration relations the measured values are $\vartheta$, $\delta$ and T, where T is the temperature of the material.

As described above with respect to the particle size measurements, the calibration coefficients for the material component ratios are determined by regression of known ratios with measurements of $\vartheta$, $\delta$ and T. The known component ratios are determined by independent analytical means on samples of the measured materials taken in the laboratory or while the apparatus is on-line. The calibration measurements for the regressions are recorded from the apparatus for the sample being sensed.

Corrections for the Presence of Shielding Walls

Since the sensors are on the outside of the container in the FIG. 1 embodiment, or behind shielding walls in the FIG. 2 embodiment, and the walls contribute to the ultrasonic phase and attenuation measurements correction may necessary. If the sensor apparatus is of the probe type shown in FIG. 2 then the dimension and orientation of the walls are fixed, and there is no need to correct the phase or attenuation values. The calibration procedure described above compensates for the constant effect of these walls. Similarly, if the clamp-on sensor apparatus of FIG. 1 is positioned on a single container type and calibrated at a fixed location, there is also no need to correct the phase or attenuation values. However, the sensor arrangement of FIG. 1 is suitable for clamp-on monitoring of materials inside containers of many different types and shapes having walls of various dimensions constructed of various materials. When used on differing containers, the phase and attentuation contributions of the shielding walls must be removed in order to determine just the attenuation and phase values for the contained material.

The invention allows correction for the walls by providing direct measurements of the total sensor separation $D_T$, the wall thickness $D_W$ and the attenuation coefficient $\alpha_W$ in the container walls. The measured total sensor separation $D_T$ is the sum of two wall thickness $D_W$ and the distance the wave travels through the filler material $D_M$:

$$D_T = 2*D_W + D_M \quad [10]$$

For the clamp-on apparatus of FIG. 1 the distance $D_T$ is measured before mounting on the container. Any suitable caliper can be used to measure this container outer diameter. For the probe configuration of FIG. 2, $D_T$ is known and specified prior to fabrication.

The wall thickness $D_W$ is calculated from the measured round-trip time $T_W$ for an ultrasonic wave that enters the outer wall and then reflects from the inner wall of the container. $D_W$ is then calculated from this time and the known sound velocity in the container wall material $c_W$. This sound velocity value for the container may be known beforehand or it can be measured separately by external means. The sound velocities of typical metal or plastic container walls do not vary significantly with frequency. For this reason, a single-frequency transit-time can be measured by any of the methods known by those skilled in the art.

The wall thickness $D_W$ is calculated from the round-trip time $T_W$ as:

$$D_W = \frac{T_W * c_W}{2} \quad [11]$$

The following equation describes the total travel time of the wave ($D_T/c_T$) as the sum of the travel time of the wave through the two walls and the travel time through the containerized material $$\frac{D_T}{c_T} = \frac{2*D_W}{c_W} + \frac{D_M}{c_M} \quad [12]$$

When the equivalent relation of equation 5 for the total phase $\vartheta_T$ measured though walls and material may be substituted into equation 12, the normalized phase for the material alone $\vartheta_M$ can be expressed as:

$$\vartheta_M = \vartheta_T + 4\pi \frac{D_W}{c_W} \quad [13]$$

Once the separation distances are known, the normalized phase in the material is calculated from equation 13 with $D_W$ substituted from equation 11.

The effects of attenuation within the container walls are compensated for in a similar way. The total attenuation coefficient $\alpha_T$ measured for the container and filler can be expressed as:

$$\alpha_T * D_T = 2 * \alpha_W * D_W + \alpha_M * D_M \quad [14]$$

where $\alpha_W$ and $\alpha_M$ are the attenuation coefficients for the wall material and contained material respectively. The attenuation coefficient for the walls may be calculated from the measured attenuation for the same round-trip wave used to determine the travel-time in the container material. Those skilled in the art will appreciate that there are many methods for determining attenuation based on the decay of the wave amplitude that is received by the sensor after multiple reflections. The attenuation coefficient for the filler is calculated from equation 14 using this measured $\alpha_W$, the known separation distances and the measurement of $\alpha_T$ described above. In this way, the phase $\vartheta_M$ and attenuation $\alpha_M$ properties of the containerized material can be measured independently of the container, and only the properties related to the monitored material used for composition determination.

Upon determination of the ultrasonic properties of the material at each selected frequency, these values may be used to determine the composition ratios, particle size and/or identity of containerized materials. For identification of the contained materials, the multi-frequency phase (or velocity) and attenuation values are measured and then matched against a database of possible filler materials. These raw values may be normalized using a number of standard techniques prior to the pattern matching. Those skilled in the art will appreciate that a number of pattern-matching methods can be applied to identify the material that best matches the measured ultrasonic properties. For example, Neural Network techniques can be used for the pattern classification and matching task.

The objects of the invention have been fully realized through the embodiments disclosed herein. Those skilled in the art will appreciate that the various aspects of the invention may be achieved through different embodiments without departing from the essential function of the invention. The particular embodiments are illustrative and not meant to limit the scope of the invention as set forth in the following claims.

What is claimed is:

1. A method of determining the composition of a material, said method comprising:
   (i) measuring an attenuation of multiple ultrasonic waves transmitted through a material at multiple frequencies;
   (ii) deriving an attenuation curve from the measured attenuations as a function of change in the ultrasonic wave frequency;
   (iii) identifying an attribute of the attenuation curve from the attenuation curve related to the composition of the material; and
   (iv) determining the composition of the material from the attribute of the attenuation curve.

2. The method of claim 1, wherein the determination of the composition of the material further comprises a determination of a mean particle size of particles in a material suspension.

3. The method of claim 1, wherein the determination of the composition of the material further comprises a determination of a size range of the largest particles in a material suspension.

4. The method of claim 1, wherein the determination of the composition of the material further comprises a determination of a component ratio of particles in a material suspension.

5. The method of claim 2, wherein the attribute of the attenuation curve identified to determine the mean particle size in the material suspension is the maximum slope of the attenuation curve near a frequency where the wavenumber ka is approximately equal to 1.

6. The method of claim 3, wherein the attribute of the attenuation curve identified to determine the size range of the largest particles in the material suspension is a width of the derivative of the attenuation curve near a frequency where the wavenumber ka is approximately equal to 1.

7. The method of claim 4, wherein the attribute of the attenuation curve identified to determine a component ratio of the particles in the material suspension is a maximum value of the attenuation curve near a frequency where the wavenumber ka is approximately equal to 1.

8. The method of claim 1, wherein the determination of the composition of the material is made from a predetermined relationship between material composition and the attribute of the attenuation curve.

9. The method of claim 1, wherein the determination of the composition of the material from the attribute of the attenuation curve further comprises comparing a known attribute of the attenuation curve for a known material to the attribute of the attenuation curve from the measured attenuation curve.

10. The method of claim 1 wherein the attribute of the attenuation curve is identified near a frequency where the wavenumber is approximately equal to 1.

11. The method of claim 1 wherein the attribute of the attenuation curve is selected from a group consisting of:
- the maximum slope of the attenuation curve near a frequency where the wavenumber ka is approximately equal to 1;
- a width of the derivative of the attenuation curve near a frequency where the wavenumber ka is approximately equal to 1; and
- a maximum value of the attenuation curve near a frequency where the wavenumber ka is approximately equal to 1.

12. The method of claim 1 wherein the identification of the attribute of the attenuation curve is made while the material is enclosed in a container.

13. An apparatus for determining the composition of a material, the apparatus comprising:
   (i) means for measuring the attenuation of multiple ultrasonic waves transmitted through a material at multiple frequencies;
   (ii) means for deriving an attenuation curve from the measured attenuations as a function of change in the ultrasonic wave frequency;
   (iii) means for identifying an attribute of the attenuation curve from the attenuation curve related to the composition of the material; and
   (iv) means for determining the composition of the material from the attribute of the attenuation curve.

14. The apparatus of claim 13, wherein the determination of the composition of the material further comprises a determination of a mean particle size of particles in a material suspension.

15. The apparatus of claim 13, wherein the determination of the composition of the material further comprises a determination of a size range of the largest particles in a material suspension.

16. The apparatus of claim 13, wherein the determination of the composition of the material further comprises a determination of a component ratio of particles in a material suspension.

17. The apparatus of claim 13, wherein the determination of the composition of the material further comprises a determination of a component ratio among multiple suspending constituents in a material suspension.

18. The apparatus of claim 13, wherein the means for measuring the attenuation of multiple ultrasonic waves comprises a first ultrasonic transducer transmitting an ultrasonic wave and a second ultrasonic transducer receiving the ultrasonic wave wherein the first ultrasonic transducer and the second ultrasonic transducer transmit and receive the ultrasonic wave at a select angle of offset relative to a line between transducer centers.

19. The apparatus of claim 13, wherein the means for measuring the attenuation of multiple ultrasonic waves comprises an ultrasonic transducer shielded from the material by a protective wall.

20. The apparatus of claim 13 wherein the attribute of the attenuation curve is identified near a frequency where the wavenumber is approximately equal to 1.

21. The apparatus of claim 13 wherein the attribute of the attenuation curve is selected from a group consisting of:
- the maximum slope of the attenuation curve near a frequency where the wavenumber ka is approximately equal to 1;
- a width of the derivative of the attenuation curve near a frequency where the wavenumber ka is approximately equal to 1; and
- a maximum value of the attenuation curve near a frequency where the wavenumber ka is approximately equal to 1.

* * * * *